US008818510B2

(12) United States Patent
Bornzin et al.

(10) Patent No.: US 8,818,510 B2
(45) Date of Patent: Aug. 26, 2014

(54) SYSTEMS AND METHODS FOR PAIRED/COUPLED PACING

(75) Inventors: Gene A. Bornzin, Simi Valley, CA (US); Joseph J. Florio, Bend, OR (US)

(73) Assignee: Pacesetter, Inc., Sylmar, CA (US)

( * ) Notice: Subject to any disclaimer, the term of this patent is extended or adjusted under 35 U.S.C. 154(b) by 967 days.

(21) Appl. No.: 12/635,474

(22) Filed: Dec. 10, 2009

(65) Prior Publication Data

US 2010/0094371 A1    Apr. 15, 2010

Related U.S. Application Data

(63) Continuation-in-part of application No. 11/929,719, filed on Oct. 30, 2007, now Pat. No. 8,706,224.

(51) Int. Cl.
*A61N 1/365* (2006.01)
(52) U.S. Cl.
USPC ............................................. 607/25; 607/114
(58) Field of Classification Search
USPC .................................. 607/9, 28; 128/696, 903
See application file for complete search history.

(56) References Cited

U.S. PATENT DOCUMENTS

| 3,857,399 A | 12/1974 | Zacouto |
| 3,939,844 A | 2/1976 | Pequignot |
| 4,674,508 A | 6/1987 | DeCote |
| 5,213,098 A | 5/1993 | Bennett et al. |
| 5,350,410 A | 9/1994 | Kleks et al. |
| 5,480,413 A | 1/1996 | Greenhut et al. |
| 5,643,327 A | 7/1997 | Dawson et al. |
| 5,792,193 A | 8/1998 | Stoop |
| 6,377,852 B1 | 4/2002 | Bornzin et al. |
| 6,501,987 B1 | 12/2002 | Lovett et al. |
| 6,968,233 B1 * | 11/2005 | Parry et al. ..................... 607/28 |
| 7,181,280 B1 | 2/2007 | Sloman |
| 7,599,739 B2 | 10/2009 | Hudnall |
| 2002/0072775 A1 * | 6/2002 | Hsu et al. ......................... 607/9 |

(Continued)

FOREIGN PATENT DOCUMENTS

| EP | 0550713 B1 | 10/1996 |
| WO | 9302745 A1 | 2/1993 |

(Continued)

OTHER PUBLICATIONS

Papageorgiou, Panos MD et al., "Coronary Sinus Pacing Prevents Induction of Atrial Fibrillation," Circulation. 1997;96:1893-1898.

(Continued)

*Primary Examiner* — Carl H Layno
*Assistant Examiner* — Erica Lee

(57) ABSTRACT

A coupled/paired stimulus pulse is delivered to the heart at an inter-pulse interval following one of i) detection of an intrinsic depolarization or ii) delivery of a primary stimulus pulse. Capture resulting from the coupled/paired stimulus pulse is sensed for. In response to capture by a coupled/paired stimulus pulse, the inter-pulse interval is incrementally decreased by a first amount until there is no capture by a coupled/paired stimulus pulse. In response to no capture by a coupled/paired stimulus pulse, the inter-pulse interval is incrementally increased by a second amount greater than the first amount, until capture by a coupled/paired stimulus pulse is detected. Once capture is again detected, paired/coupled pacing is delivered at the inter-pulse interval which resulted in capture for a predetermined period of time or until loss of capture occurs.

14 Claims, 9 Drawing Sheets

(56) References Cited

U.S. PATENT DOCUMENTS

| | | |
|---|---|---|
| 2003/0074029 A1 | 4/2003 | Deno et al. |
| 2004/0049118 A1 | 3/2004 | Ideker et al. |
| 2004/0049235 A1 | 3/2004 | Deno et al. |
| 2005/0090872 A1 | 4/2005 | Deno et al. |
| 2006/0247698 A1* | 11/2006 | Burnes et al. ............ 607/9 |

FOREIGN PATENT DOCUMENTS

| | | |
|---|---|---|
| WO | 0158518 A2 | 8/2001 |
| WO | 0158518 A3 | 8/2001 |
| WO | 02053026 A2 | 7/2002 |
| WO | 02053026 A3 | 7/2002 |
| WO | 02053228 A1 | 7/2002 |
| WO | 03020364 A2 | 3/2003 |

OTHER PUBLICATIONS

Siddons, Harold and Sowton, Edgar, Cardiac Pacemakers. 1967:201-216.

* cited by examiner

SYSTEMS AND METHODS FOR PAIRED/COUPLED PACING

CROSS REFERENCE TO RELATED APPLICATIONS

This application is a continuation-in-part of U.S. patent application Ser. No. 11/929,719, filed Oct. 30, 2007, now U.S. Pat. No. 8,706,224 titled "Systems and Methods for Paired/Coupled Pacing and Dynamic Overdrive/Underdrive Pacing."

FIELD OF THE INVENTION

The invention generally relates to implantable cardiac stimulation devices such as pacemakers and implantable cardioverter defibrillators (ICDs), and in particular, to techniques for pacing heart tissue involving paired/coupled pacing.

BACKGROUND OF THE INVENTION

It has long been known that a stimulus may be delivered about 300 ms following a primary pacing pulse or about 300 ms following a spontaneous depolarization. These stimuli have the effect of electrically depolarizing the heart but typically they do not induce a separate mechanical myocardial contraction. Instead, they extend or enhance the strength and/or duration of the contraction already induced by a primary pacing pulse. This phenomena is known as pulseless electrical activity (PEA).

When a secondary pulse is delivered about 300 ms following a primary pacing pulse, this is referred to as paired pacing. When a spontaneous depolarization triggers a pacing pulse about 300 ms later, this is referred to as coupled pacing. Coupled pacing has the ability to prolong the refractory period and affects a slowing of the heart by increasing the interval between spontaneous depolarizations. Performing paired pacing also prolongs the refractory period and allows pacing the heart at a rate slower than the intrinsic rate, because the prolonged refractory period delays the spontaneous depolarization.

Many uses for paired/coupled pacing techniques have been proposed. Siddons and Sowton (*Cardiac Pacemakers*. 1967: 201-216) have proposed that paired/coupled pacing may be used to provide continuous extra-systolic augmentation and indeed cardiac performance has been found to be enhanced by this therapy. The objective is to treat heart failure and to enhance cardiac performance in congestive heart failure (CHF). It proved to be effective in these patients but there was great concern that an extra-stimulus provided in the ventricles at an inappropriate time, i.e., during the relative refractory period, would create excessive arrhythmic risk, particularly fibrillation. Such patients are already susceptible to arrhythmias and may be put at an even greater risk by stimulating near the vulnerable period.

Coupled pacing has also been used for treatment of ventricular and atrial tachyarrhythmias in which a stimulus is coupled to a spontaneous depolarization and set to a fraction of the spontaneous cardiac interval as taught by Zacouto (U.S. Pat. No. 3,857,399) and Pequignot (U.S. Pat. No. 3,939,844). This effectively slows the heart during an arrhythmia.

Paired pacing has been proposed in the atrium to augment ventricular contraction but was not found to be as effective as paired ventricular stimulation. Bornzin et al. (U.S. Pat. No. 6,377,852) has proposed that paired stimulation of the atrium may be used to increase the atrial refractory period and prevent premature atrial contractions (PACs) from the left atrium (LA) from triggering reentrant atrial arrhythmias. This technique may be especially effective during LA pacing since it has been shown that inducing atrial arrhythmias from the right atrium is very difficult. Papageorgiu showed that pacing from distal coronary sinus (CS) caused low atrial depolarization rendering it refractory to premature stimuli delivered from HRA and precluded induction of atrial fibrillation. (Papageorgiu et al. "Coronary sinus pacing prevents induction of atrial fibrillation," CIRC, 1997; 96:1893-1989.) Bornzin has also suggested that paired pacing in the atrium may be used to slow the overall rate to allow more time for filling the ventricle, which may be useful in enhancing stroke volume in patients with diastolic dysfunction. The following patents and patent applications also discuss paired pacing and related techniques: U.S. Pat. No. 5,213,098 to Bennett et al.; U.S. Patent Application 2003/0074029 of Deno et al.; and U.S. Patent Application 2004/0049235 of Deno et al.

None of the foregoing patents or publications, however, provides effective techniques for safely stimulating the heart just outside of the relative refractory period so as to obtain improved cardiac performance through extra-systolic augmentation, with reduced risk of fibrillation induction. It is to this end that aspects of the invention are particularly directed.

SUMMARY OF THE INVENTION

In one aspect of the invention, an improvement is provided for use within an implantable cardiac stimulation device capable of performing paired pacing. The improvement comprises the delivery of paired pacing with an interval set sufficient to ensure that an evoked response associated with a secondary pulse is wider than an evoked response associated with a primary pulse of the pair of pulses. By timing the secondary pulse in such a manner, improved hemodynamic performance can be achieved, e.g. improved left ventricular (LV) pressure can be achieved and an improved change in pressure with time (dP/dt) can also be achieved. The improved inter-pulse interval may be advantageously employed whenever paired pacing is appropriate, in either the ventricles or the atria.

This aspect of the invention is also applicable to coupled pacing. With coupled pacing, a "secondary" pulse is delivered subsequent to an intrinsic depolarization, rather than subsequent to a primary pacing pulse. As with paired pacing, coupled pacing can prolong the refractory period and cause a slowing of heart rate by increasing the interval between spontaneous depolarizations. When applied to coupled pacing, the improvement of the invention comprises the delivery of coupled pacing with an interval set sufficient to ensure that an evoked response associated with a coupled pulse is wider than the preceding intrinsic depolarization. By timing the coupled pulse in this manner, improved hemodynamic performance can also be achieved. The improved coupling interval is advantageously employed whenever coupled pacing is otherwise appropriate.

In other aspects, the invention relates to a method of controlling an inter-pulse interval for delivering paired or coupled pacing to a heart. In one such aspect, a coupled/paired stimulus pulse is delivered to the heart at an inter-pulse interval following one of i) detection of an intrinsic depolarization or ii) delivery of a primary stimulus pulse. Capture resulting from the coupled/paired stimulus pulse is sensed for. In response to capture by a coupled/paired stimulus pulse, the inter-pulse interval is incrementally decreased by a first amount until there is no capture by a coupled/paired stimulus pulse. In response to no capture by a coupled/paired stimulus pulse, the inter-pulse interval is incrementally increased by a second amount greater than the first amount, until capture by a coupled/paired stimulus pulse is detected. Once capture is again detected, paired/coupled pacing is delivered at the inter-pulse interval which resulted in capture for a predetermined period of time or until loss of capture occurs.

Other aspects, features, and advantages of the invention will be apparent from the detailed description that follows in the combination with the attached drawings. Method, system and apparatus embodiments of the invention are also provided.

BRIEF DESCRIPTION OF THE DRAWINGS

The above and further features, advantages and benefits of the invention will be apparent upon consideration of the present description taken in conjunction with the accompanying drawings, in which.

DESCRIPTION OF THE PREFERRED EMBODIMENTS

Figure 1:
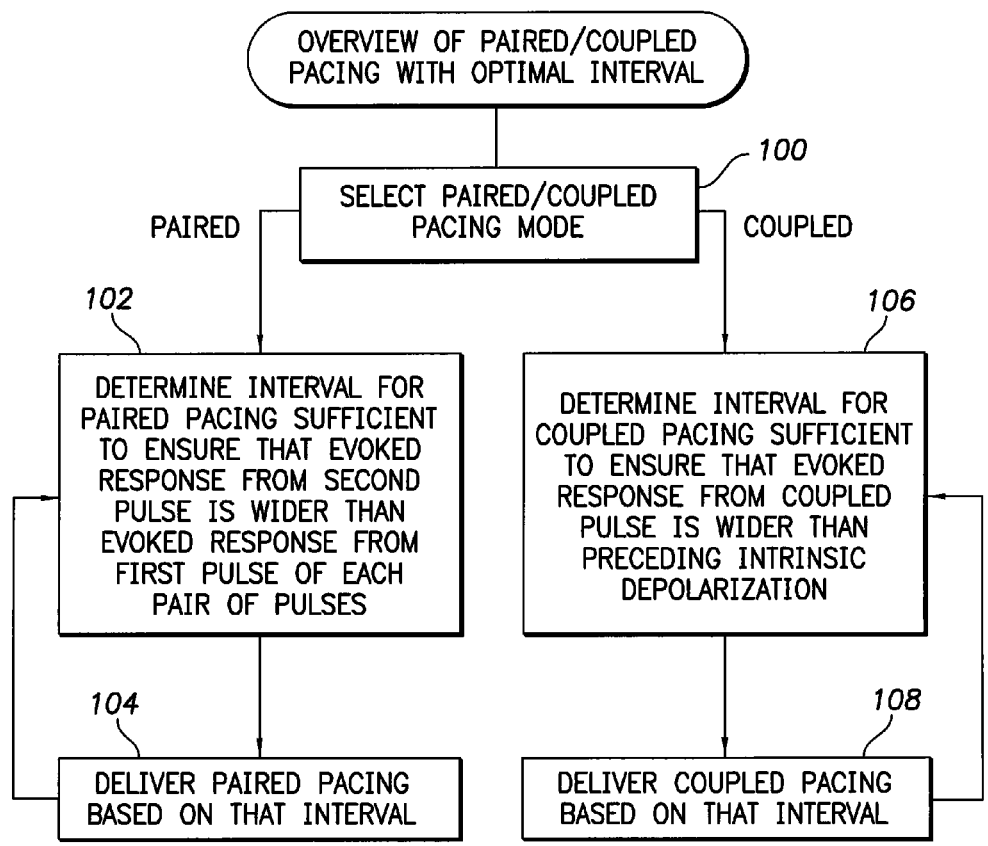
FIG. 1 is a flow diagram providing an overview of a technique for performing paired/coupled pacing with an optimal inter-pulse interval.

The following description includes the best mode presently contemplated for practicing the invention. This description is not to be taken in a limiting sense but is made merely for the purpose of describing the general principles of the invention. The scope of the invention should be ascertained with reference to the issued claims. In the descriptions that follow, like numerals or reference designators will be used to refer to like parts or elements throughout.

As noted above, paired pacing is a pacing technique whereby a secondary pacing pulse is delivered shortly following a primary pacing pulse. The primary pulse triggers both an electrical depolarization (i.e., an evoked response) of myocardial tissue and a corresponding mechanical contraction. The secondary pulse, if properly timed, electrically depolarizes the myocardial tissue, typically does not induce a mechanical myocardial contraction, and instead extends or enhances the strength and/or duration of the contraction already induced by a primary pulse. The affect of the secondary pulse is referred to as pulseless electrical activity (PEA). Coupled pacing is a pacing technique whereby a pacing pulse is delivered shortly after detection of a spontaneous depolarization, i.e., an intrinsic depolarization. As with paired pacing, if the coupled pace is properly timed, PEA results.

Paired/coupled pacing can prolong the refractory period associated with myocardial depolarization so as to permit pacing the heart at a rate slower than the intrinsic rate by delaying spontaneous depolarizations. It can also improve cardiac performance.

Note that, with paired pacing, the paired pulses are typically both delivered using the same electrode within the same chamber of the heart, e.g. both are delivered via a right ventricular (RV) tip electrode. This is in contrast with cardiac resynchronization techniques (CRT) wherein a pair of pulses is delivered using different leads in different chambers of the heart. Typically, with CRT, a pair of pulses is delivered separately in the left and right ventricles. The inter-pulse delay between the RV pulse and the LV pulse is set to ensure that both pulses achieve both an electrical depolarization and a corresponding mechanical contraction. With paired pacing, as noted, the timing between the pulses is preferably set so that the second pulse of the pair triggers PEA.

Several techniques are described below for carefully and automatically timing the delivery of the pacing pulse so as to place it just outside of the relative refractory period. Optimizing the inter-pulse delay to this end, protects a patient from the potential of inducing an arrhythmia.

In accordance with one technique, a sensed evoked response, i.e., electrical depolarization, following a paired or coupled pacing pulse provides an indication of when to optimally provide a paired or coupled stimulation. Stimulating too early following a primary paced event (in the case of paired pacing) or an intrinsic depolarization (in the case of coupled pacing), during the absolute refractory period, results in no detectable evoked response and thus is not a suitable time for the second stimulus. Stimulating a little later during the relative refractory period triggers a small, subnormal size evoked response. Finally stimulating a little later, immediately beyond the relative refractory period results in a substantially full size evoked response.

Turning now to FIG. 1, an embodiment of this technique for optimizing inter-pulse delay for use with paired pacing or coupled pacing is described. "Inter-pulse delay" or "inter-pulse interval", as used herein means, in the case of paired pacing, the time between the primary pulse and secondary pulse, and, in the case of coupled pacing, the time between the intrinsic depolarization and the coupled pulse. Beginning at step 100, the implanted device selects either paired pacing or coupled pacing in accordance with the needs of the patient and the programming of the device. If paired pacing is selected then, beginning at step 102, the device first determines the inter-pulse interval for paired pacing sufficient to ensure that an evoked response from a second pulse of the pair of pulses is wider than the evoked response from the first pulse of the pair of pulses. It is believed that this inter-pulse interval is optimal because it provides a somewhat prolonged refractory period, which is beneficial for many applications, including dynamic overdrive/underdrive pacing. Any suitable measure of the width of the evoked response may be used, such as the duration during which the absolute magnitude of the evoked response exceeds some predetermined voltage. In one specific technique, a paced depolarization integral (PDI) is employed to help quantify the width of each evoked response. PDI is discussed in U.S. Pat. No. 5,643,327 to Dawson, et al., which is incorporated herein by reference.

The determination of step 102 may be made, for particular patient, by adjusting the inter-pulse interval through a range of values while measuring and comparing the width of the associated evoked responses. The value of the inter-pulse interval that provides the longest width for the evoked response of the second pulse relative to the evoked response of the first pulse is then stored in the implantable device for subsequent use during paired pacing. The optimal interval may depend upon the pacing rate. Hence, the optimization procedure may be repeated for different pacing rates with different optimal values determined and stored for use with different ranges of pacing rates. Alternatively, a single value may be determined for use at a base pacing rate, and then adjusted by the implanted device based upon the amount by which the current pacing rate exceeds the base rate. Experimentation may be performed to determine an appropriate adjustment factor. Depending upon the particular implementation, optimal inter-pulse interval values may be determined during an initial programming session between physician and patient or, if the device is so equipped, the device itself may periodically perform an optimization procedure to update the optimal interval values within the patient so as to automatically compensate for any physiological or anatomical changes within the patient, such as changes resulting from progression of heart disease. Alternatively, the interval between first and second pulses can be set to the shortest duration that ensures that the second pulse does not trigger a mechanical contraction of a chamber of the heart to which it is applied. Then, at step 104, the device begins delivering paired pacing pulses using the interval determined at step 102. Paired pacing may be performed in accordance with otherwise conventional paired pacing techniques.

Alternatively, if coupled pacing is to be performed then, beginning at step 106, the device determines the inter-pulse interval for coupled pacing sufficient to ensure that the evoked response from the coupled pulse is wider than the intrinsic depolarization. It is believed that this coupling interval is optimal because it provides the longest combined refractory period, which is beneficial for many applications. Again, any appropriate technique may be employed for quantify the width of the intrinsic depolarization. The determination of the optimal coupling interval may be made, for a particular patient, by adjusting the coupling interval through a range of values while measuring the width of both the intrinsic depolarization and the evoked response of the coupled pulse. This interval is adjusted until the evoked response from the coupled pulse is found to be wider than the intrinsic depolarization to which it is coupled. The value of the inter-pulse interval that provides the longest width for the evoked response of the coupled pulse relative to the width of the intrinsic depolarization is the optimal interval and is stored in the implantable device for subsequent use during coupled pacing.

Similar to paired pacing, the optimal interval associated with coupled pacing may depend upon the intrinsic rate, with higher interest rates typically necessitating a shorter coupling interval. Hence, the coupling interval optimization procedure may be repeated for different intrinsic rates with different optimal values determined and stored for use with different ranges of intrinsic rates. Alternatively, a single value may be determined for use at a rest pacing rate, and then adjusted by the implanted device based upon the amount by which the current intrinsic rate exceeds the rest rate. Experimentation may be performed to determine an appropriate adjustment factor. In addition, as with paired pacing, depending upon the particular implementation, optimal coupling interval values may be determined during an initial programming session or, if the device is so equipped, the device itself may periodically perform an optimization procedure to update the optimal coupling values within the patient. In any case, beginning at step 108, the device then begins delivering coupled pacing using the interval determined at step 106.

Thus, FIG. 1 summarizes an optimization technique for determining an optimal or preferred inter-pulse delay for paired pacing or an optimal or preferred coupling interval for coupled pacing. The optimal intervals may generally be used whenever paired or coupled pacing would otherwise be deemed appropriate, subject to physician approval.

Figure 2A:
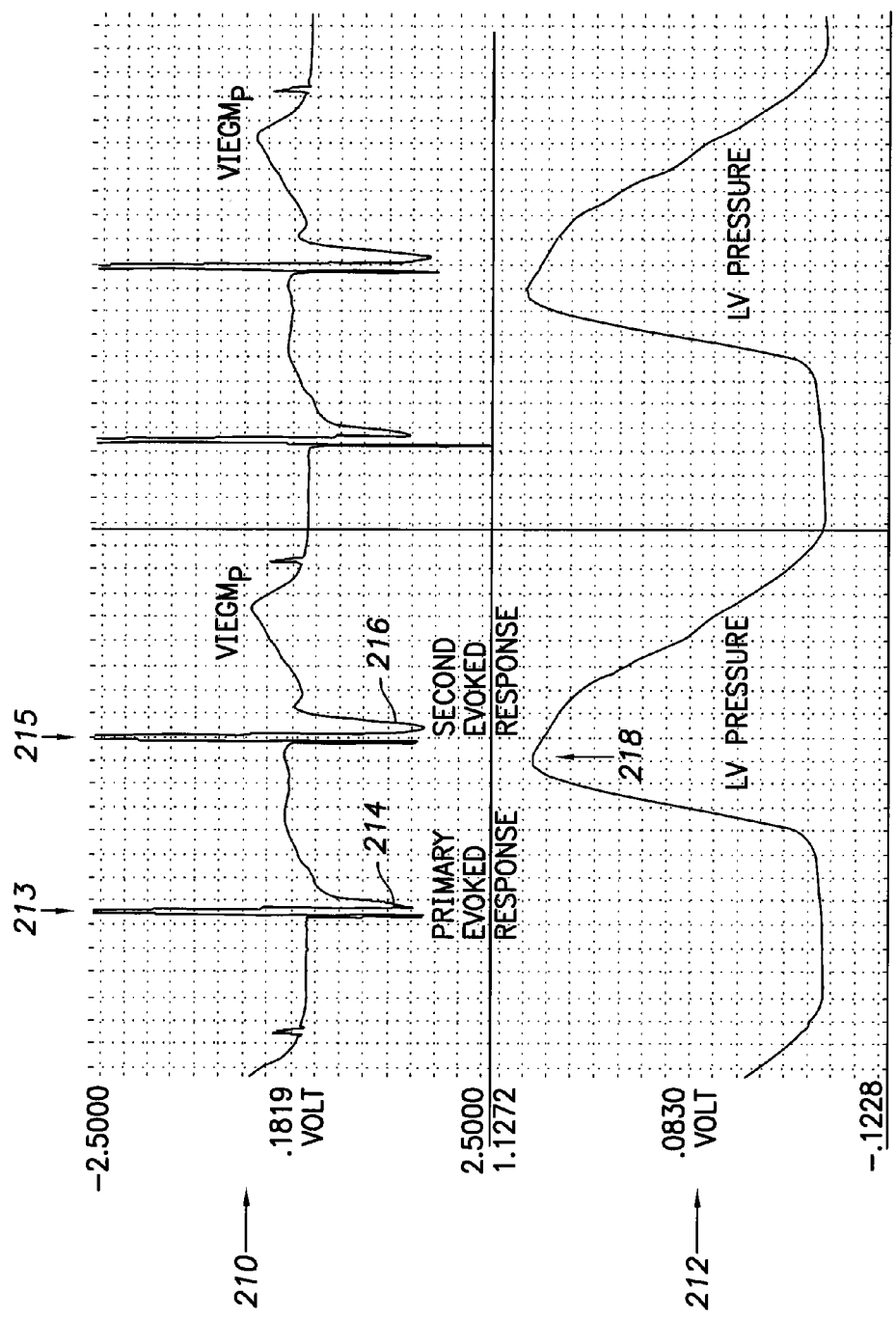
FIG. 2A is a diagram of exemplary ventricular IEGM traces and LV pressure traces, particularly illustrating the use of optimal inter-pulse intervals during paired pacing, in accordance with the general techniques of FIG. 1.
Figure 2B:
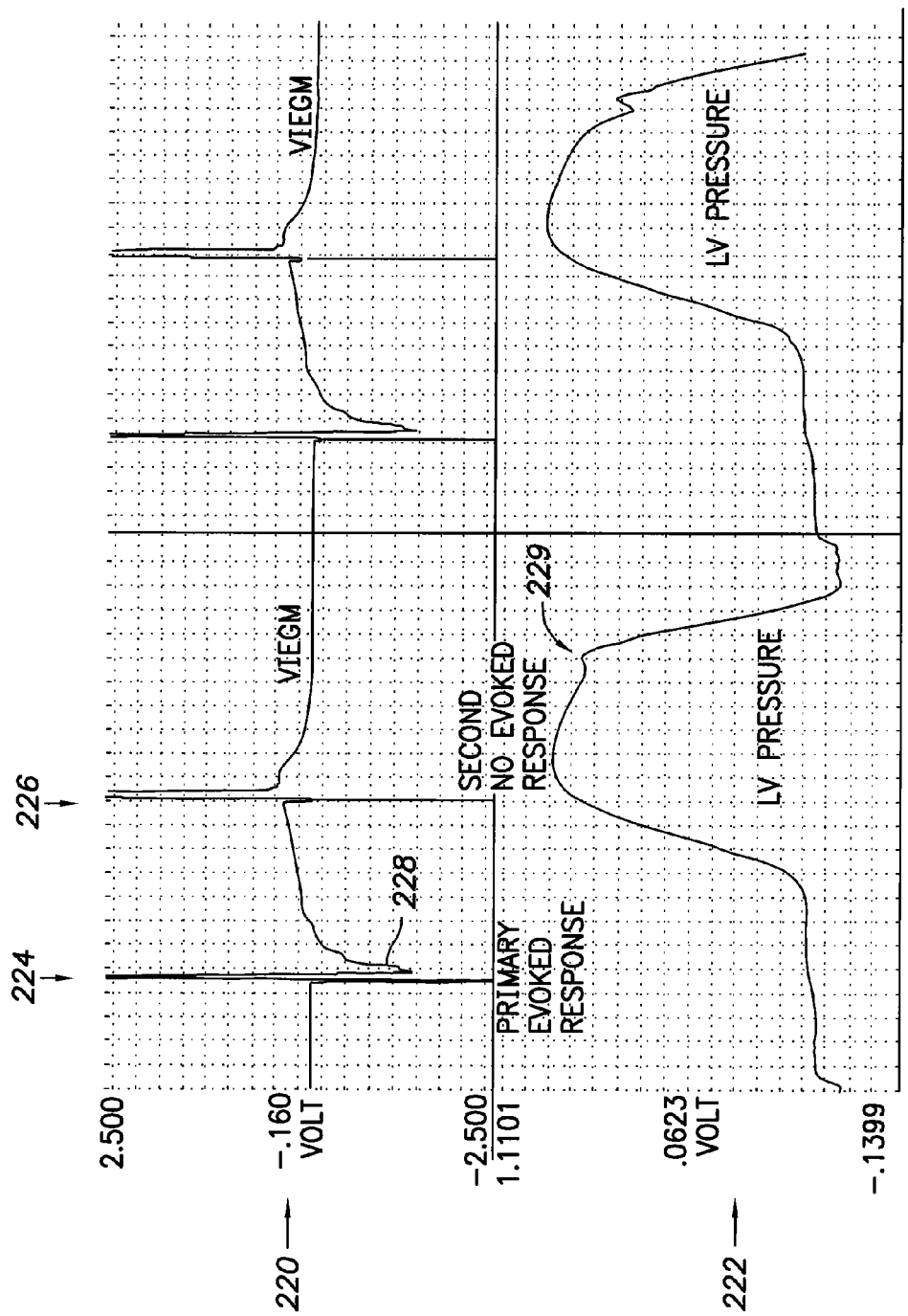
FIG. 2B is a diagram of exemplary ventricular IEGM traces and LV pressure traces, particularly illustrating circumstances wherein a second pulse of a pair of pulses fails to capture.
Figure 2C:
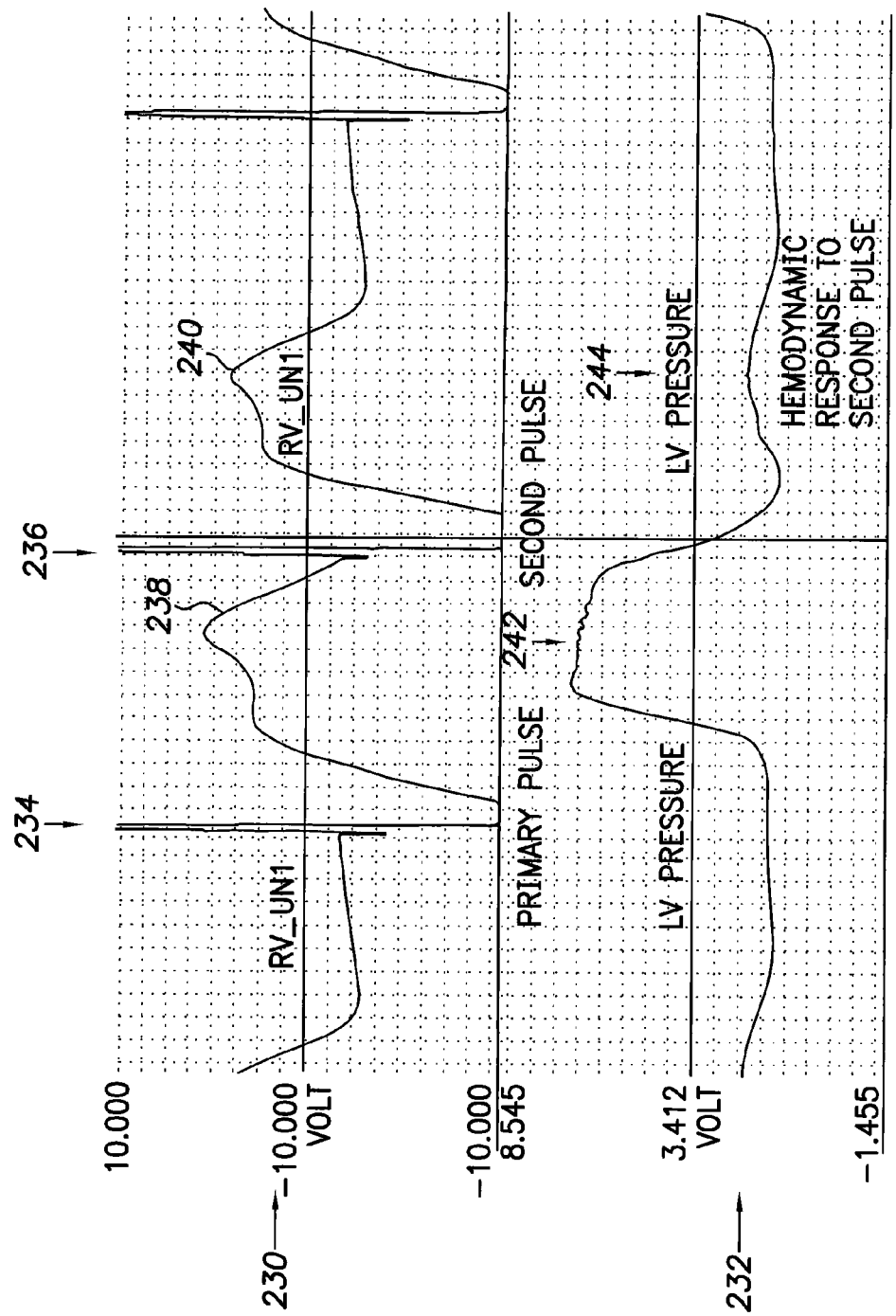
FIG. 2C is a diagram of exemplary ventricular IEGM traces and LV pressure traces, particularly illustrating the use of a non-optimal inter-pulse interval during paired pacing, resulting in a separate hemodynamic response triggered by the secondary pulse.

The effects of the optimization technique of FIG. 1 are illustrated within FIGS. 2A-2C. Referring first to FIG. 2A, a ventricular IEGM trace 210 is shown alongside a trace of LV pressure 212 for an example involving paired pacing. In this example, the inter-pulse interval is optimized in accordance with techniques of FIG. 1 to ensure that the evoked response associated with the second pulse of the pair is wider than that of the primary pulse. The evoked response of a primary pulse 213 is identified by reference 214; the evoked response of a secondary pulse 215 is denoted by reference from 216. The LV pressure profile resulting from the paired pulses exhibits only a single high peak 218, indicative of effective ventricular pumping. This is in contrast with traces of FIG. 2B, which illustrates a circumstance in which the second pulse of the pair of pulses fails to capture because it is delivered too soon, i.e. the inter-pulse interval is too short. More specifically, FIG. 2B illustrates a ventricular IEGM trace 220 along with a corresponding LV pressure trace 222 for a pair of pulses 224 and 226 delivered subject to an inter-pulse interval, which is too short. The first pulse evokes a response, denoted by reference 228. The second pulse, however, fails to evoke a response. Hence, the (nonexistent) evoked response of second pulse is not wider than the evoked response of the first pulse, causing degradation in the left ventricular pressure profile. As can be seen, the LV pressure profile has a peak magnitude less than that of FIG. 2A and includes a notch followed by a secondary peak 229, indicative of non-optimal ventricular pumping, possibly due to asynchronous contractions of the left and right ventricles or other ventricular dyssynchronies.

FIG. 2C illustrates an example wherein the second pulse is properly captured but the inter-pulse interval is too long. Again, a pair of traces is illustrated—including a ventricular IEGM trace 230 and a LV pressure trace 232. A pair of ventricular pulses 234 and 236 is delivered subject to an inter-pulse interval, which is too long. Primary pulse 234 triggers an evoked response 238; whereas secondary pulse 236 triggers a second evoked response 240. The resulting profile in LV pressure exhibits a first peak 242 followed by a shallower, secondary peak 244 representative of the hemodynamic response of the ventricles to the second pulse. As a result of the failure of the ventricles to contract optimally, the peak ventricular pressure is lower than that of FIG. 2A. Also, the area (or integral) of the overall ventricular pressure curve is smaller, typically indicating less blood pumped during the beat.

Although FIG. 2A is illustrative of the benefits of paired pacing pulses, similar benefits may be found when applying the width-based technique to coupled ventricular pacing pulses as well. Also, although the traces illustrated in FIGS. 2A-2C are derived from test subjects under clinical conditions, similar benefits are expected to be achieved within actual patients under real-world conditions.

Thus, FIGS. 1-2C illustrate techniques for use with paired/coupled pacing pulses for achieving improvements in LV pressure by optimizing the paired/coupled pacing interval.

Figure 3:
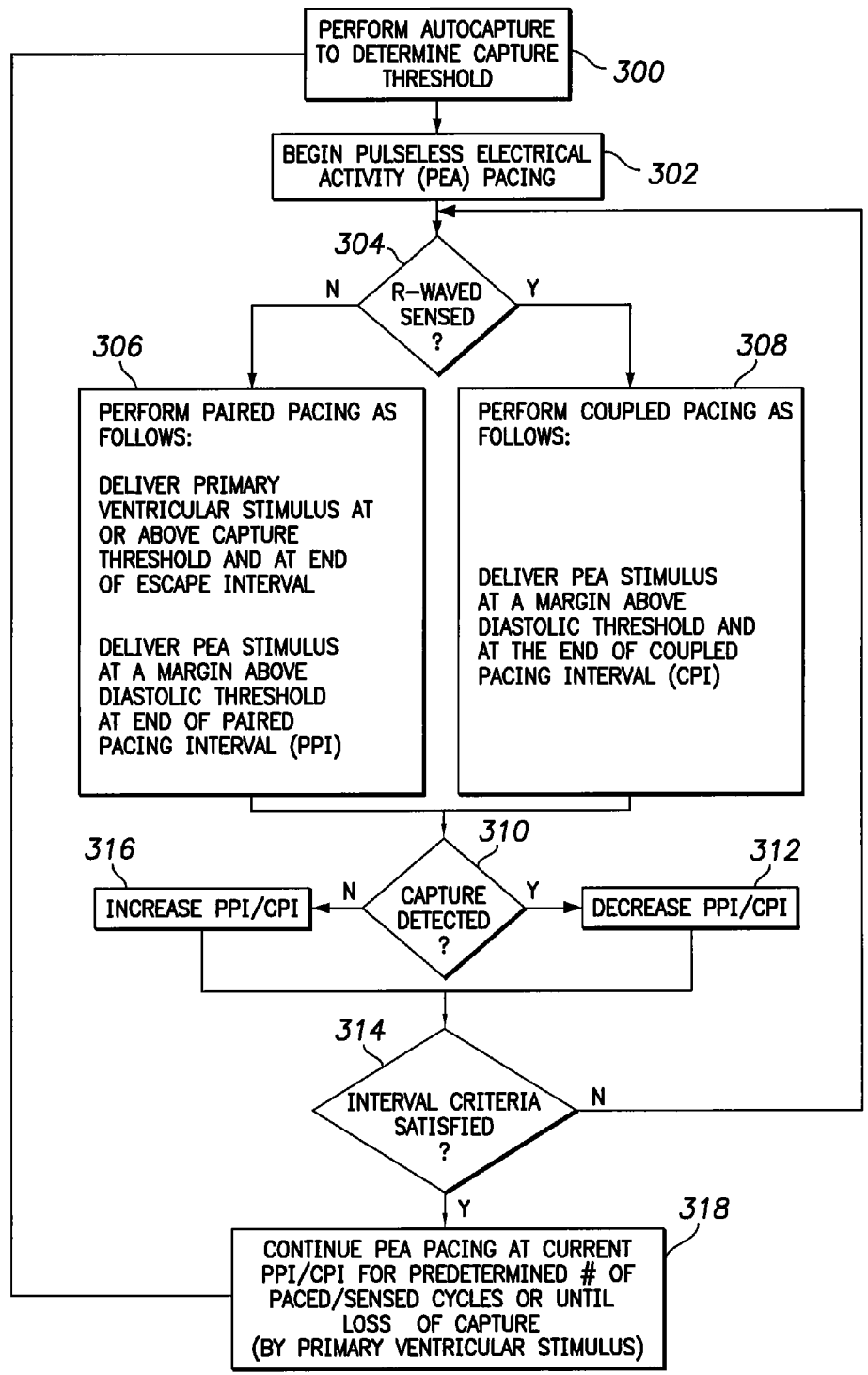
FIG. 3 is a flow diagram of a technique for controlling the inter-pulse interval during paired or coupled pacing of a heart.

Turning now to FIG. 3, another technique for optimizing inter-pulse delay for use with paired pacing or coupled pacing is described. Beginning at step 300, capture detection is performed by an implanted medical device to determine the pulse amplitude in either voltage or current, at a given, fixed pulse width, needed to effectuate capture of cardiac tissue. Alternatively, the pulse duration may be changed at a given amplitude. This pulse amplitude is referred to as the "capture threshold," and is typically a factor above the "diastolic threshold." To ensure capture, a safety margin may be added to the capture threshold, in which case subsequent electrical stimuli would be delivered with an amplitude greater than the determined capture threshold. A margin may be, for example, 0.125 volts. Methods of performing capture detection are well known in the art. One exemplary method is described in U.S. Pat. No. 7,181,280, titled "System and Method of Automatically Adjusting Auto Capture Safety Margin," the contents of which are herein incorporated by reference.

At step 302, pulseless electrical activity (PEA) pacing in initiated. This pacing may be performed periodically or on a continuous basis. PEA pacing may comprise paired pacing or coupled pacing depending on whether an intrinsic ventricular depolarization is sensed at step 304. If an intrinsic ventricular depolarization is not sensed, pair pacing is performed at step 306. During paired pacing a primary stimulus pulse having an amplitude sufficient to effectuate capture of cardiac tissue is delivered at the end of an escape interval. This amplitude may correspond to the capture threshold or to the capture threshold plus safety margin as determined by a capture detection process.

Soon after delivery of the primary stimulus pulse, a PEA stimulus pulse, i.e., a paired pulse or a secondary stimulus pulse, having an amplitude in excess of the diastolic threshold is delivered. The amplitude of the secondary stimulus pulse is typically not much greater than that of the diastolic threshold and may be, for example, 1.05 to 3 times the diastolic threshold. The inter-pulse interval between the primary stimulus pulse and the PEA stimulus pulse is referred to as the paired pacing interval (PPI) and is typically in the range of 200-300 ms. Ideally, the amplitude of the paired PEA stimulus pulse and length of the PPI are such that delivery of the paired PEA stimulus pulse will prolong electrical depolarization and enhance mechanical myocardial contraction.

Figure 4:
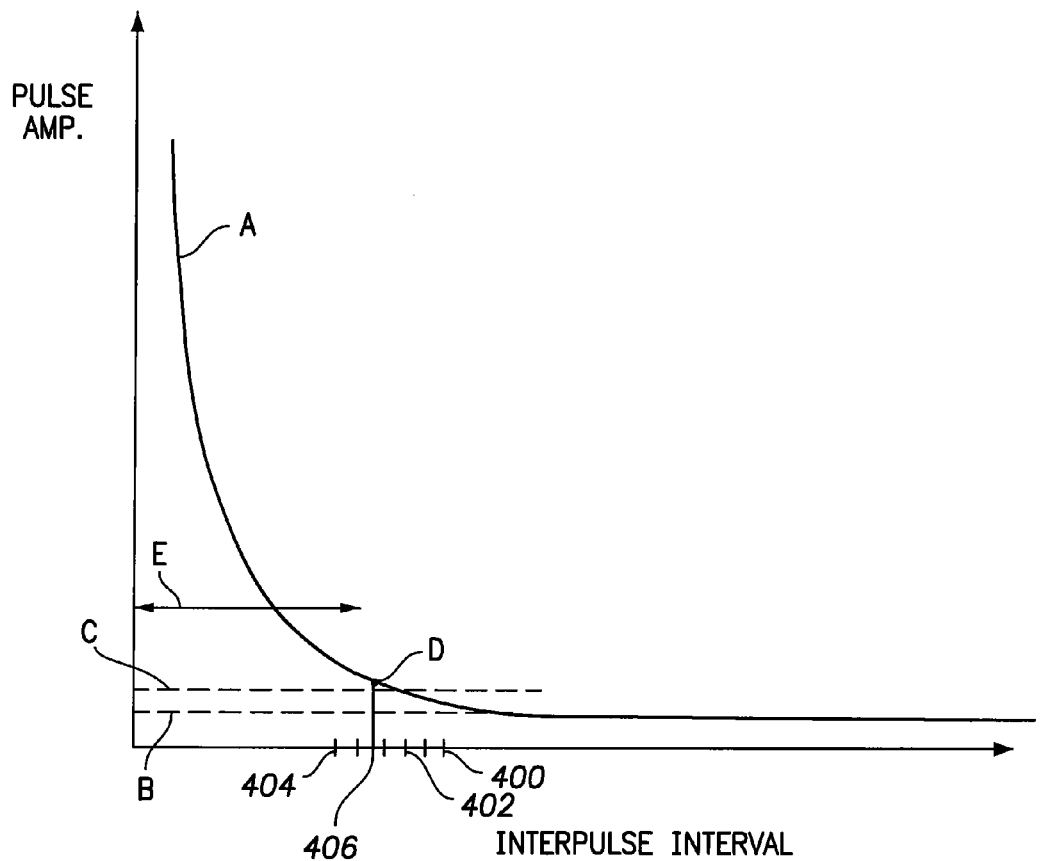
FIG. 4 is illustrates a cardiac tissue capture curve A as a function of extrastimulus intervals (x axis) and energy (y axis)

The effect of the increased amplitude of the PEA stimulus pulse may be understood with reference to FIG. 4, which illustrates a cardiac tissue capture curve A as a function of extrastimulus intervals (x axis) and voltage or current pulse amplitude (y axis). Note that the pulse amplitude required to capture cardiac tissue remains quite constant at long extrastimulus intervals but rises at shorter intervals. The substantially constant, flat portion of the curve corresponds to the diastolic threshold. In accordance with the invention, the amplitude of the PEA stimulus C is chosen to be slightly above the diastolic threshold B. As will become evident from the continued description of the process of FIG. 3, the increased level of PEA stimulus amplitude, in combination with pacing interval adjustments, allows the process to hone in on a spot D that is within a portion of the curve A that is just outside of the relative refractory period E. A stimulus delivered at the PEA stimulus amplitude and at the optimal pacing interval produces the desired outcome—electrical depolarization of the heart with enhancement of the mechanical myocardial contraction induced by the primary stimulus pulse.

Returning to step 304, if an intrinsic ventricular depolarization is detected, then coupled pacing is performed at step 308. Coupled pacing involves the delivery of a PEA stimulus pulse, i.e., a coupled pulse or a secondary stimulus pulse, soon after detection of an intrinsic ventricular depolarization. As with the paired PEA pulse, the pulse amplitude of the coupled PEA pulse slightly exceeds the diastolic threshold and may be, for example, between 1.05 to 3 times the diastolic threshold.

The inter-pulse interval between the intrinsic depolarization and the coupled PEA stimulus pulse is referred to as the coupled pacing interval (CPI) and is typically in the range of 200-300 ms. Ideally, the amplitude of the coupled PEA stimulus pulse and length of the CPI are such that delivery of the coupled PEA stimulus pulse will electrically depolarize the heart and enhance the mechanical myocardial contraction induced by the primary stimulus pulse without inducing a separate contraction.

Continuing with FIG. 3, the effect of the PEA stimulus (paired or coupled, as the case may be) is monitored for at step 310. If the PEA stimulus induces capture (depolarization plus mechanical contraction), for example at PPI/CPI 400 in FIG. 4, the PPI/CPI is decreased by an amount x (e.g., 2-10 ms) at step 312. At this point, capture does not satisfy an "optimal pacing interval criteria" (defined further below) at step 314 and the process returns to step 304. The process repeats until the effect of the PEA stimulus is monitored again at step 310. If the PEA stimulus again induces capture, for example at PPI/CPI 402 in FIG. 4, the current PPI/CPI is decreased by an amount x at step 312 and the process returns to step 304. This process continues until capture is no longer detected at step 310, which may occur, for example, when the PPI/CPI is at 404.

When capture is no longer detected at step 310, the process increases the current PPI/CPI at step 316 by an amount y, where y is greater than x. In one embodiment, y is a multiple of x. For example, y may be 2(x) or 3(x). If an "optimal pacing interval criteria" (defined further below) is not met at step 314, the process returns to step 304 and repeats until the effect of the PEA stimulus is monitored again at step 310. This process continues until capture is detected at step 310, which may occur, for example, when the PPI/CPI is at 406. Satisfaction of an optimal pacing interval criteria may occur, for example, when the PEA pacing process transitions from a no capture state, e.g., FIG. 4, point 404, to a capture state, e.g., FIG. 4, point 406, at step 310.

After this optimal PPI/CPI is determined, at step 318, PEA stimuli are delivered at the optimal PPI/CPI for a predetermined number of paced or sensed cardiac cycles or until there is loss of capture by a primary pacing pulse during paired pacing, or an intrinsic depolarization is not sensed during couple pacing. In either of these cases, the process returns to step 300.

The preceding process may be considered a means for providing "safe paired pacing" that uses a variation on autocapture. In this situation, autocapture may be enabled with 0.125 volt precision to establish the late diastolic threshold at about 60 to 90 ppm, which is the conventional pacing threshold at which primary ventricular stimuli are delivered. When the paired pulse or coupled pulse is delivered at the primary ventricular stimuli voltage threshold plus a margin, e.g., 0.125 V, the stimulus may capture and a large evoked response may be detected. However if the paired pulse or coupled pulse is delivered too soon in the relative refractory period, the stimulus will not capture and this will be evident because there will be no evoked response. This may be viewed as a protective mechanism and it can also be used to establish a means of safely stimulating just outside of the relative refractory period during the PEA interval, with a safe low amplitude pulse.

In another paired/coupled pacing technique, control of the inter-pulse interval for paired or coupled pacing is enhanced using a sensor that provides measurements of cardiac mechanical activity, independent of measurements of cardiac electrical activity, i.e., evoked response/capture detection through IEGM analysis. Various mechanical-activity sensors may be used including: heart sounds from a microphone, a mechanical electrical detector, a pressure sensor on a lead, an impedance signal from the ventricle, an extra cardiac impedance signal, e.g., between the SVC coil and case, a PPG sensor, or an accelerometer. In general terms, the measurements of cardiac mechanical activity are used to confirm that the secondary pulse did enhance or extend the cardiac mechanical contraction induced by a primary pacing pulse and that enhancement is optimal.

Figure 5:
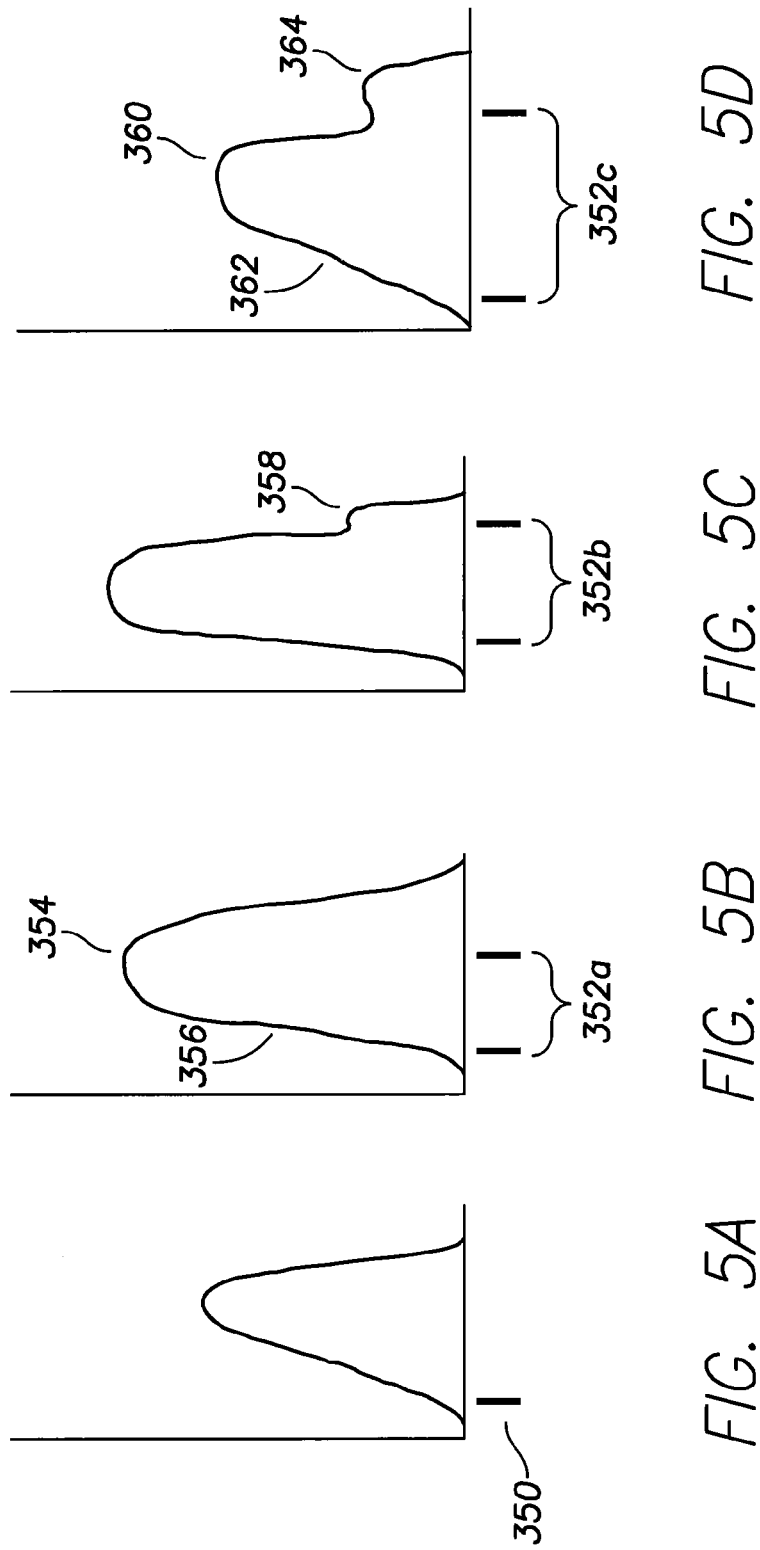
FIG. 5A-5D depicts various LV pressure profiles corresponding to different pacing conditions, including single pacing and paired pacing.

FIGS. 5A-5D, depict a series of cardiac mechanical activity responses, e.g., LV pressure profiles, under different pacing conditions. The first LV profile (FIG. 5A) is a control response resulting from delivery of a single pacing pulse 350. The second, third and fourth LV profiles (FIGS. 5B, 5C and 5D), result from delivery of paired pacing pulses 352a, 352b, 352c, at slightly increasing paired pacing intervals (PPI). The second LV profile (FIG. 5B) exhibits several improved characteristics over that of the control response (FIG. 5A), including an increased initial peak amplitude 354 and an increased slope 356. The third LV profile (FIG. 5C) also exhibits improved characteristics relative to the control response (FIG. 5A). It does, however, include a slight secondary peak 358 indicative of possible non-optimal ventricular pumping. The fourth LV profile (FIG. 5D) exhibits characteristics less desirable than those of the second and third, including a decreased peak amplitude 360, decreased slope 362 and a pronounced secondary peak 364, indicative of greater non-optimal ventricular pumping relative to the third LV profile.

In operation, measurements provided by the mechanical-activity sensor are used in conjunction with the evoked response/capture detection provided by cardiac electrical activity analysis, for example as described above with reference to FIG. 3. In one configuration, upon determination of an optimal PPI/CPI in accordance with the evoked response/capture process of FIG. 3, the mechanical-activity measurements resulting from that optimal PPI/CPI are analyzed to determine if cardiac mechanical activity is also optimal. If the mechanical activity is acceptable, as described above with reference to the LV profiles in FIG. B and FIG. 5C, the optimal PPI/CPI is confirmed. If, however, the mechanical activity is less than acceptable, for example as described above with reference to the LV profile in FIG. 5D, the PPI/CPI is adjusted. Such adjustment may involve decreasing the PPI/CPI by an amount x, reconfirming evoked response/capture detection and then again checking for acceptable mechanical activity.

A determination as to what is acceptable and less than acceptable mechanical cardiac activity may be derived through an algorithm training process, wherein a patient's changes in mechanical activity measurements at different PPI/CPI intervals are processed to arrive at patient-specific criteria. For example, in the case of LV pressure profiles, a minimum acceptable slope or minimum peak amplitude or combination thereof may define patient-specific thresholds, above which a measurement is deemed acceptable.

It should be noted that the value of a PPI and CPI for a given patient will most likely be different, accordingly, the determination of these respective intervals are maintained as separate processes. For example, although the algorithm of FIG. 3 describes both paired and coupled processes, the algorithm operates in only one of a paired pacing or couple pacing scenario based on whether an intrinsic ventricular depolarization is sensed. If a condition at step 304 changes from coupled pacing, i.e., one where an intrinsic ventricular depolarization is sensed, to paired pacing, i.e., one where an intrinsic ventricular depolarization is not sensed, the algorithm stores previously determined coupled pacing intervals, proceeds with paired coupled pacing processing and, should the condition change from paired pacing back to coupled pacing, retrieves the for stored coupled pacing intervals and proceeds with coupled pacing processing. Paired pacing intervals are likewise stored and retrieved.

Exemplary Pacer/ICD

Figure 6:
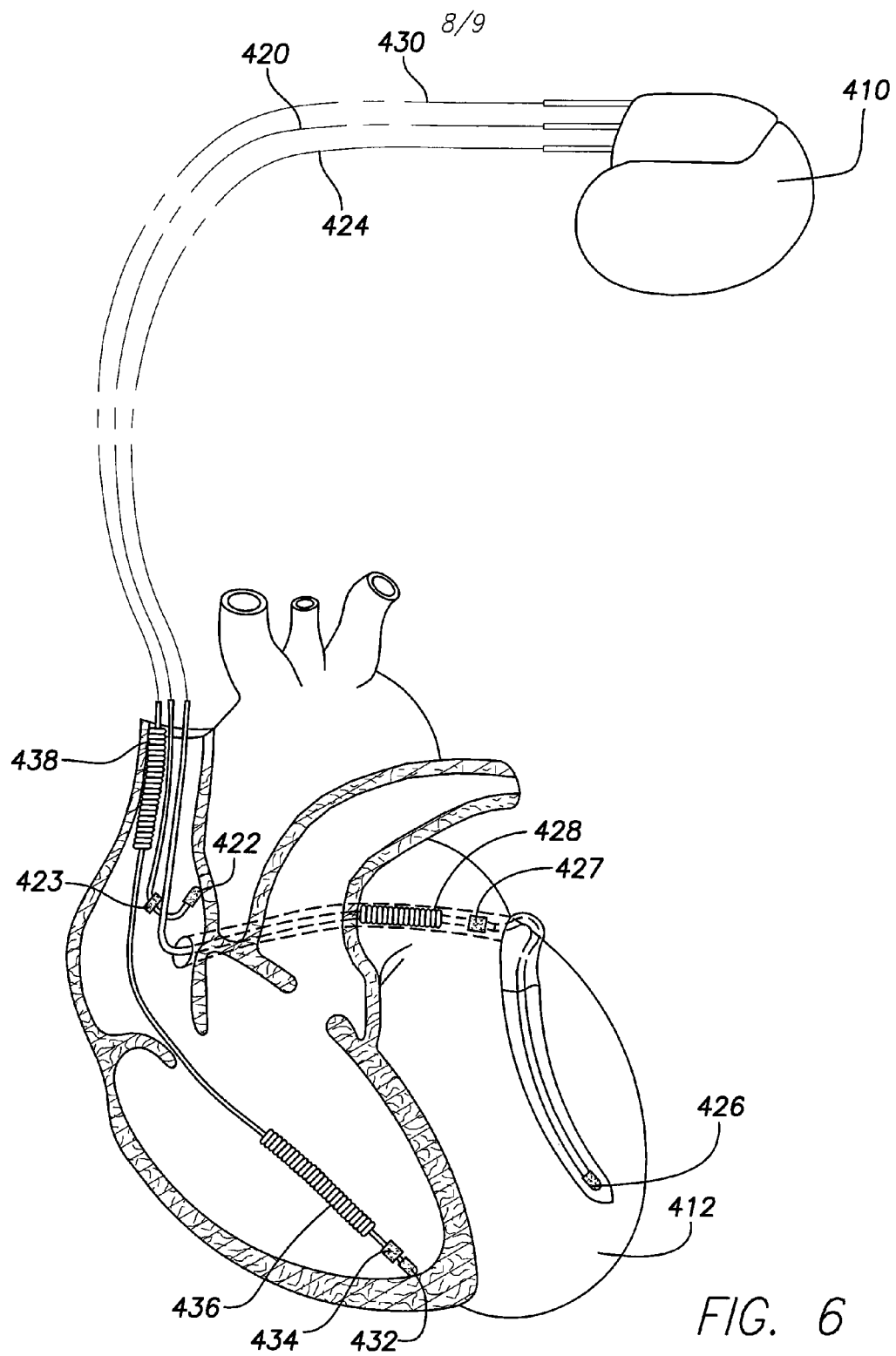
FIG. 6 is a simplified diagram illustrating an implantable stimulation device, equipped to perform the techniques of FIGS. 1, 3 and 4, with leads implanted into the heart of a patient.

For the sake of completeness, a description of an exemplary pacer/ICD will now be provided, which is capable of implementing the aforementioned pacing techniques. FIG. 6 provides a simplified block diagram of a pacer/ICD 410, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart 412 by way of a left atrial lead 420 having an atrial tip electrode 422 and an atrial ring electrode 423 implanted in the atrial appendage. Pacer/ICD 410 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 6, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 7:
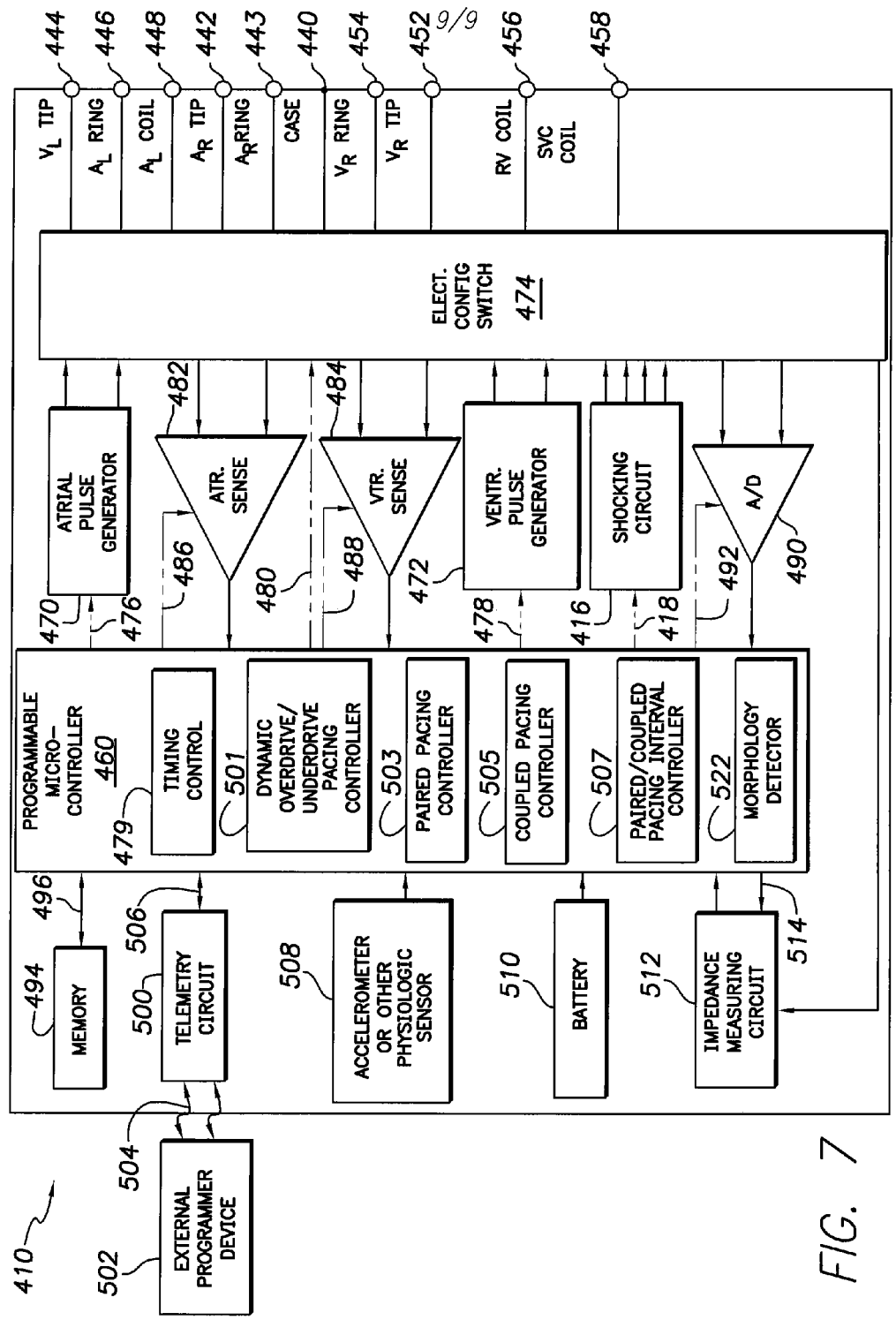
FIG. 7 is a functional block diagram of the device of FIG. 6 illustrating basic elements of the device and particularly illustrating components for providing pulseless electrical activity stimulation in accordance with the techniques of FIGS. 1, 3 and 4.

A simplified block diagram of internal components of pacer/ICD 410 is shown in FIG. 7. While a particular pacer/

ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 410, shown schematically in FIG. 7, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 7, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 460 or memory 494) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV/PV delay, V-V Delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

Insofar as paired/coupled pacing is concerned, the microcontroller includes a dynamic overdrive/underdrive pacing controller 501, a paired pacing controller 503, a coupled pacing controller 505 and a paired/coupled pacing interval controller 507. These units operate in accordance with the techniques described above. Although shown as being part of the microcontroller, these units may instead be implemented as components separate from the microcontroller.

The pacer/ICD additionally includes a battery 510, which provides operating power to all of the circuits shown in FIG. 7. The battery 510 may vary depending on the capabilities of pacer/ICD 410. If the system only provides low voltage therapy, a lithium iodine or lithium copper fluoride cell may be utilized. For pacer/ICD 410, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 410 is preferably capable of high voltage therapy and appropriate batteries.

As further shown in FIG. 7, pacer/ICD 410 is shown as having an impedance measuring circuit 512 which is enabled by the microcontroller 460 via a control signal 514. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 410 is intended to operate as an implantable cardioverter/defibrillator (ICD) device, it detects the occurrence of an arrhythmia, and, if so programmed, automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Preferably, during AF, dynamic ventricular overdrive/underdrive pacing with paired pacing pulses is performed, as discussed above. Should a cardioversion shock be desired, perhaps because AF does not terminate within an acceptable period of time, the device deactivates dynamic ventricular overdrive/underdrive pacing and instead delivers the cardioversion shock. Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as WI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval.

VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

What have been described are various techniques for paired/coupled pacing and dynamic overdrive/underdrive pacing. Although described primarily with reference to an example wherein the implanted device is an ICD, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method of controlling an inter-pulse interval for delivering paired or coupled pacing to a heart, said method comprising:
    a) delivering a coupled/paired stimulus pulse to the heart at an inter-pulse interval, in connection with pulseless electrical activation (PEA), following one of i) detection of an intrinsic depolarization or ii) delivery of a primary stimulus pulse, wherein the primary stimulus pulse is sufficient to capture cardiac tissue;
    b) sensing for capture resulting from the coupled/paired stimulus pulse;
    c) in response to capture by a coupled/paired stimulus pulse, decrementing the inter-pulse interval by a first amount until there is no capture by a coupled/paired stimulus pulse, wherein the inter-pulse interval is set to prolong depolarization without inducing a separate contraction; and
    d) in response to no capture by a coupled/paired stimulus pulse, incrementing the inter-pulse interval by a second amount greater than the first amount, until capture by a coupled/paired stimulus pulse is again detected.

2. The method of claim 1 further comprising:
    e) delivering coupled/paired pacing at the inter-pulse interval at which capture is again detected in step d), until loss of capture or for a predetermined number of cardiac cycles, whichever occurs first; and
    thereafter, repeating a) through d).

3. The method of claim 1 wherein the amplitude of the coupled/paired stimulus pulse is greater than a diastolic threshold.

4. The method of claim 3 wherein the amplitude of the coupled/paired stimulus pulse is in the range of 1.05 to 3 times greater than the diastolic threshold.

5. The method of claim 1 wherein the first amount is in the range of 2-10 ms and the second amount is in the range of 2 to 3 times the first amount.

6. The method of claim 1 wherein sensing for capture comprises measuring evoked responses.

7. The method of claim 1 further comprising:
    e) obtaining measurements of cardiac mechanical activity corresponding to capture by a coupled/paired pacing pulse;
    f) processing the cardiac mechanical activity measurements to determine whether the mechanical activity is acceptable.
    g) if the mechanical activity is not acceptable, decreasing the inter-pulse interval by a first amount;
    h) delivering a coupled/paired stimulus pulse at the decreased inter-pulse interval; and
    i) sensing for capture resulting from the coupled/paired stimulus pulse; and
    j) if capture by the coupled/paired stimulus pulse is detected, repeating e) through i).

8. The method of claim 1, wherein the inter-pulse interval is set such that the coupled/paired stimulus pulse is timed to trigger PEA.

9. An implantable medical device that automatically controls an inter-pulse interval for delivering paired/coupled pacing pulses to a heart, said device comprising:
    a sensor configured to sense cardiac depolarizations;
    a pulse generator configured to deliver stimulation pulses to cardiac tissue; and
    a controller operatively coupled to the sensor and pulse generator and configured to:
    a) in the absence of a sensed intrinsic depolarization, cause the pulse generator to deliver a primary stimulus pulse to the heart, wherein the primary stimulus pulse amplitude is sufficient to capture cardiac tissue;
    b) cause the pulse generator to deliver a coupled/paired stimulus pulse to the heart at an inter-pulse interval, in connection with pulseless electrical activation (PEA), following one of i) detection of an intrinsic depolarization or ii) delivery of the primary stimulus pulse;
    c) sense for capture resulting from the coupled/paired stimulus pulse;
    d) in response to capture by a coupled/paired stimulus pulse, decrementing the inter-pulse interval by a first amount until there is no capture by a coupled/paired stimulus pulse, wherein the inter-pulse interval is set to prolong depolarization without inducing a separate contraction; and
    e) in response to no capture by a coupled/paired stimulus pulse, incrementing the inter-pulse interval by a second amount greater than the first amount, until capture by a coupled/paired stimulus pulse is detected.

10. The device of claim 9 wherein the controller is further configured to:
    f) deliver coupled/paired pacing at the inter-pulse interval at which capture is again detected in step e), until loss of capture or for a predetermined number of cardiac cycles, whichever occurs first; and
    thereafter, repeat a) through e).

11. The device of claim 9 wherein the amplitude of the coupled/paired stimulus pulse is greater than a diastolic threshold.

12. The device of claim 9 wherein the first amount is in the range of 2-10 ms and the second amount is in the range of 2 to 3 times the first amount.

13. The device of claim 9 further comprising a mechanical sensor configured to provide measurements indicative of cardiac mechanical activity corresponding to capture by a coupled/paired pacing pulse, and wherein the controller is further configured to:
    f) obtain measurements of cardiac mechanical activity from the mechanical sensor;
    g) process the cardiac mechanical activity measurements to determine whether the mechanical activity is acceptable.

h) if the measurement is not acceptable, decrease the inter-pulse interval by a first amount;
i) deliver a coupled/paired stimulus pulse at the decreased inter-pulse interval; and
j) sense for capture resulting from the coupled/paired stimulus pulse; and
k) if capture by the coupled/paired stimulus pulse is detected, repeat f) through j).

14. The device of claim 9, wherein the inter-pulse interval is set such that the coupled/paired stimulus pulse is timed to trigger PEA.

\* \* \* \* \*